(12) United States Patent
Rice et al.

(10) Patent No.: US 7,027,150 B1
(45) Date of Patent: Apr. 11, 2006

(54) APPARATUS FOR MEASURING THE CONCENTRATION OF A SPECIES AT A DISTANCE

(75) Inventors: Steven F. Rice, Oakland, CA (US); Mark D. Allendorf, Fremont, CA (US)

(73) Assignee: Sandia National Laboratories, Livermore, CA (US)

( * ) Notice: Subject to any disclaimer, the term of this patent is extended or adjusted under 35 U.S.C. 154(b) by 97 days.

(21) Appl. No.: 10/877,630

(22) Filed: Jun. 24, 2004

(51) Int. Cl.
*G01N 21/64* (2006.01)

(52) U.S. Cl. ................................... 356/318; 250/458.1
(58) Field of Classification Search ................. 356/318
See application file for complete search history.

(56) References Cited

OTHER PUBLICATIONS

Damm et al, Excimer laser fragmentaton-fluorescence spectroscopy as a method for monitoring ammonium nitrate and ammonium sulfate particles, Chemosphere, vol. 42, issue 5-7, Feb. 2001, pp. 655-661.*
Gottwald et al, Simultaneous detection of nickel and potassium in the flue gas of a fluidised bed coal combustor by excimer laser-induced fragmentation fluorescence, Fuel Processing Technology, vol. 80, issue, 2, Feb. 15, 2003, pp. 143-153.*
Monkhouse et al, Phase discrimination of alkali species in PCFB combustion flue gas using simultaneous monitoring by surface ionisation and photofragmentation fluorescence, Fuel, vol. 82, issue 4, Mar. 4, 2003, pp. 365-371.*

\* cited by examiner

*Primary Examiner*—F. L. Evans
(74) *Attorney, Agent, or Firm*—Timothy P. Evans

(57) ABSTRACT

Corrosion of refractory silica brick and air quality issues due to particulate emissions are two important glass manufacturing issues that have been tied to sodium vapor and its transport throughout the melt tank. Knowledge of the relationship between tank operating conditions and tank atmosphere sodium levels are therefore important considerations in correcting corrosion and air quality issues. However, until recently direct quantitative measurements of sodium levels has been limited to extractive sampling methods followed by laboratory analysis. Excimer laser induced fragmentation (ELIF) fluorescence spectroscopy is a technique that permits the measurement of volatilized NaOH in high temperature environments on a timescale of less than one second. The development of this method and the construction of field-portable instrumentation for glass furnace applications are herein disclosed. The method is shown to be effective in full-scale industrial settings. Characteristics of the method are outlined, including equipment configuration, detection sensitivity, and calibration methodology.

15 Claims, 9 Drawing Sheets

ID: 7,027,150 B1

APPARATUS FOR MEASURING THE CONCENTRATION OF A SPECIES AT A DISTANCE

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND

Over the past several years there have been a number of reports illustrating the use of an online analytical technique to monitor metals in industrial process gas (see for instance Monkhouse, P.: "On-line diagnostic methods for metal species in industrial process gas", *Prog. Energy Combust Sci.* 28 (2002) pp. 331–381). One method that has been demonstrated to be particularly promising is photo-fragmentation fluorescence ("PFF") of which Excimer Laser Induced Fragmentation Fluorescence ("ELIF") is a variant that utilizes the high-energy ultraviolet light from an excimer laser as the excitation source. To date, a number of authors have explored the use of ELIF in industrial applications specifically to determine alkali concentrations in solid fuel combustors (K. J. Rensberger Welland, et al., *Appl. Opt.* 32 (1993) pp. 4066–4073; K. T. Hartinger, et al., *Proc. Comb. Inst.* 25 (1994) pp. 193–199; B. L. Chadwick, et al., *Anal. Chem.* 67 (1995) pp. 710–716; F. Greger, et al., *Proc. Comb. Inst.* 26 (1996) pp. 3301–3307; P. G. Griffin, et al., *Rev. Sci. Instrum.* 69 (1998) pp. 3874–3677; and U. Gottwald, et al., *Appl. Phys. B* 69 (1999) pp. 151–154). This prior work has shown that this method is capable of detecting sodium hydroxide and sodium chloride concentrations in the part per billion range ("ppb") at temperatures as high as 1000° C.

The general technical approach of the method is to illuminate the atmosphere that contains simple molecular metal-containing species, such as NaOH, NaCl, KOH, etc., with a pulse of laser light (in this case with a 193-nm beam from an argon fluoride (ArF) excimer laser). The subsequent photo-dissociation results in a population of excited metal atoms that produce one or more atomic fluorescence lines that are easily detected.

There are a number of potential applications of this nearly real-time analytical technique in addition to solid fuel combustion diagnostics. In our case, understanding the behavior of alkali metals in glass furnaces is an especially attractive application because of two important practical issues surrounding the role of sodium in the atmosphere of a glass-making furnace. Sodium volatilization from the melt to the vapor phase in the furnace and into the exhaust can directly effect the formation of particulates and indirectly affect the durability of the furnace over time. This may be especially true for furnaces operating with pure oxygen in place of air in the burners.

Given the important role alkali vapor plays in practical operation of furnaces, it is desirable to make direct measurements of alkali metal concentration within the furnace atmosphere. All recent thermodynamic studies of the relevant chemistry of volatilized alkali metals indicate that greater than 99% of the sodium or potassium in the furnace atmosphere exist in the form of a metal hydroxide vapor, i.e., as either NaOH or KOH. All currently practical, analytical methods for measuring sodium and potassium in glass furnaces are performed using extractive sampling followed by analysis of the hot vapor, of a liquid condensate, or of both. In contrast, the present application is drawn to a method and an apparatus for providing real time data that can be used to optimize furnace operation.

SUMMARY

In the instant application, we illustrate the use of ELIF as a means for examining the concentration of alkali metals in the gas composition of glass manufacturing furnaces. We report here the development of a measurement method and the design and implementation of an apparatus that can measure the concentration of NaOH in the vapor phase of an oxygen-fuel glass furnace in real-time in an industrial environment. The principle of operation of the spectroscopy-based sensor and several examples of the application of a field-ready unit are described. The present disclosure shows that although precise and absolute quantitative measurements are difficult using the present instrument configuration, a sensor based on the ELIF approach has the potential to provide real time information when calibrated with extractive sampling.

The optical probe of the present embodiment comprises a lens system for focusing an incident light beam onto a plurality of analysis locations within a flow stream being monitored and for collecting light returning from each of the plurality of analysis locations. The optical probe also includes means for separating the incident light beam from the return light beam whereby the return light beam can be transformed to provide a real-time analysis of material present at each of the analysis locations.

DETAILED DESCRIPTION OF THE EMBODIMENTS

Figure 1:
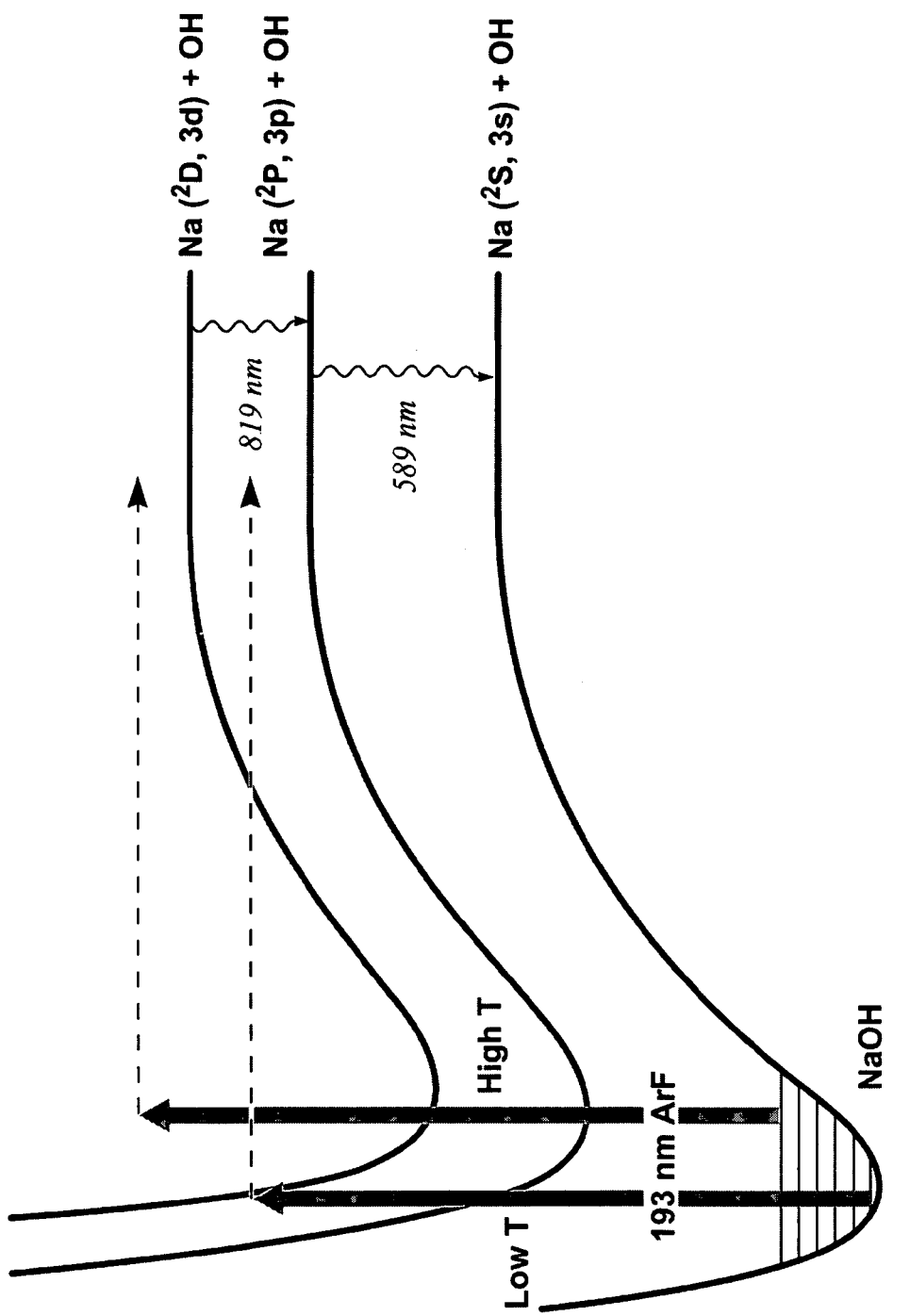
FIG. 1 shows the potential curves showing the application of ELIF for the detection of NaOH in high-temperature environments.

Herein disclosed is an apparatus for quantitatively monitoring the amount of sodium in the atmosphere above a bath of molten glass in an industrial glass-making furnace, or any similarly challenging environment. The basic physical process providing for the detection of sodium concentration via ELIF is illustrated by FIG. 1. The well-known technique relies on the detection of atomic fluorescence from electronically excited sodium atoms that are produced from the dissociation of NaOH by 193-nm ultraviolet light generated by an ArF excimer laser. (see for instances Gottwald, et al., Appl. Phys. B v. 69, (1999) pp. 151–154). Excitation of ground-state NaOH at 193 nm contains sufficient energy to produce Na atoms in an excited $^2P$ state. The excited $^2P$ atoms subsequently emit light at 589 nm, which is in the middle of the visible spectrum. This fluorescence is actually composed of two lines separated by 0.6 nm and are known as the sodium "D" lines.

In a high-temperature environment, a portion of the NaOH molecular population contains sufficient vibrational energy such that when excited by 193 nm light, sodium atoms are additionally in an excited atomic state identified as a $3d^2D$ state. This state can transition to the $3p^2P$ state, emitting radiation at 819 nm. Depending on the furnace conditions, both the 589-nm and 819-nm lines can be observed. The 589-nm line is present in the ELIF spectrum of numerous simple Na-containing molecular species whereas the observation of 819 nm $^2D-^2P$ fluorescence is species and temperature dependent.

Figure 2:
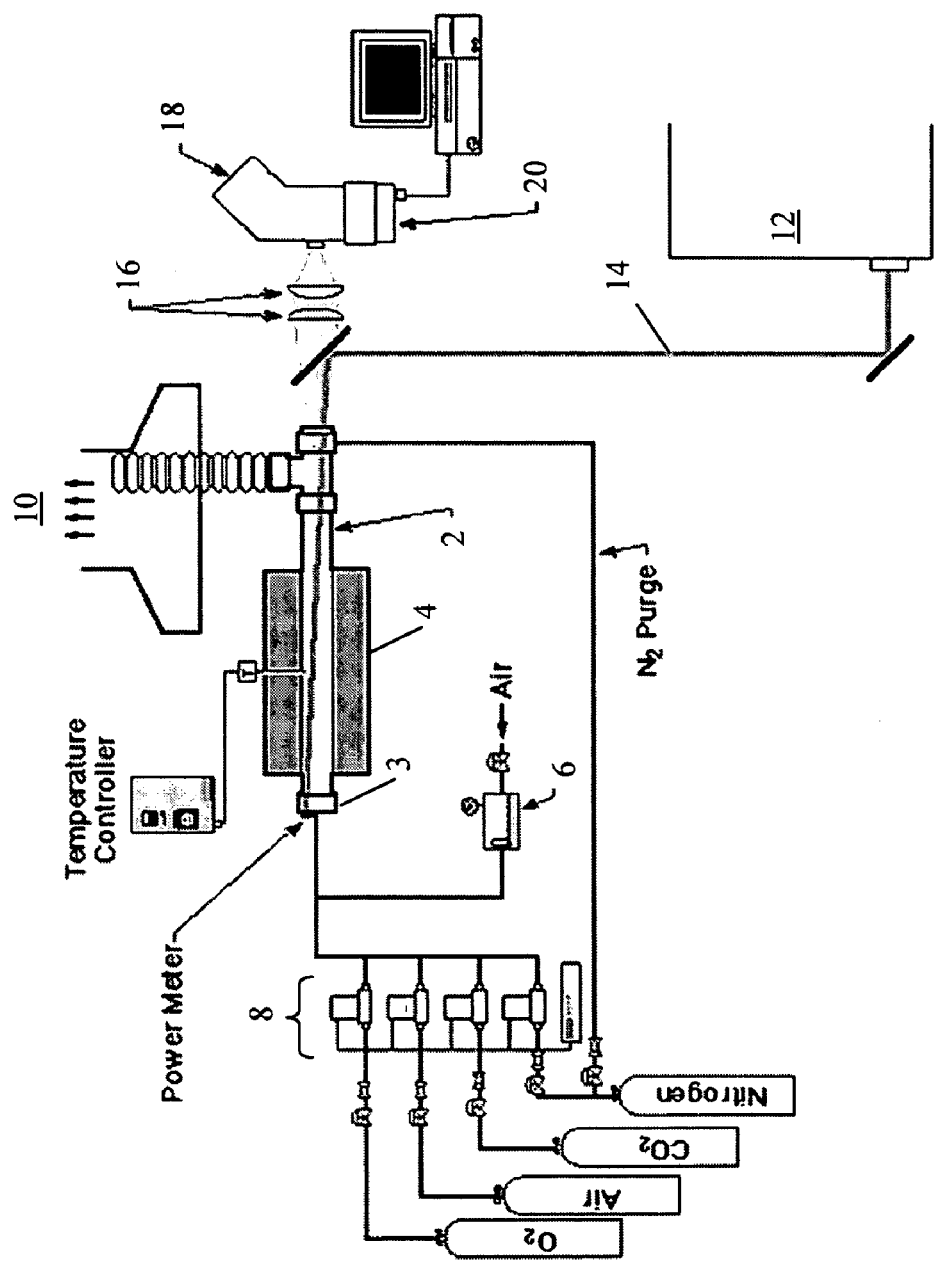
FIG. 2 shows a schematic of the experimental layout used to characterize the detection of NaOH using the ELIF method.

The keys to the design of a practical instrument capable of quantitatively measuring NaOH concentration in situ in a glass-making furnace rests on the characteristics of the ELIF signal as a function of laser power, laser penetration depth into the furnace, temperature, and gas composition in the furnace atmosphere. FIG. 2 shows a schematic of the experimental layout used to characterize NaOH concentration in situ when using the ELIF method. In particular, a 1-meter long, 5 cm OD, alumina tube 2 is disposed within a high temperature tube furnace 4. Ceramic tube 2 is equipped with UV fused silica windows 3 that serve as optically transparent end-caps. Atomizer 6 produces a flow of water vapor containing NaOH aerosol that is simultaneously introduced into the tube furnace with other gases from a mixing manifold 8 such that the mixture passes through the tube furnace and is vented into a fume hood 10.

The atomizer was calibrated to establish the water vapor flow rate. This flow rate and the NaOH concentration in the reservoir is used to determine the mass flow rate of sodium into the tube. (In addition to the NaOH carried by the water vapor, the composition of the gas in the flow cell can include carbon dioxide, nitrogen, and oxygen to better mimic the furnace environment.)

Excimer laser 12 generates laser beam 14 which is directed into ceramic tube 2 after a slow flow of the desired gas mixture has been established. The laser is operated at 100 Hz and produces a 12 ns pulse. The 193-nm ultraviolet light from the excimer dissociates the NaOH species in the vapor phase and produces sodium atoms that can subsequently fluoresce at several wavelengths in the visible range. This light is collected with a telescopic lens system 16, dispersed by a small spectrometer 18, and detected using a multi-channel light detection means 20 such as an intensified multi-channel diode array or similar charge coupled device array ("CCD") such as a multi-channel intensified CCD array.

Figure 3A:
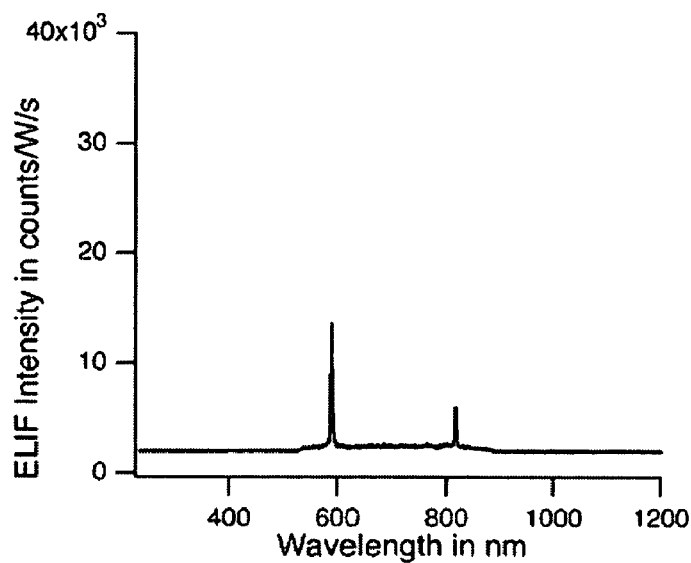
FIG. 3 shows a typical ELIF signal at 1500° C. and at 1000° C.
Figure 3B:
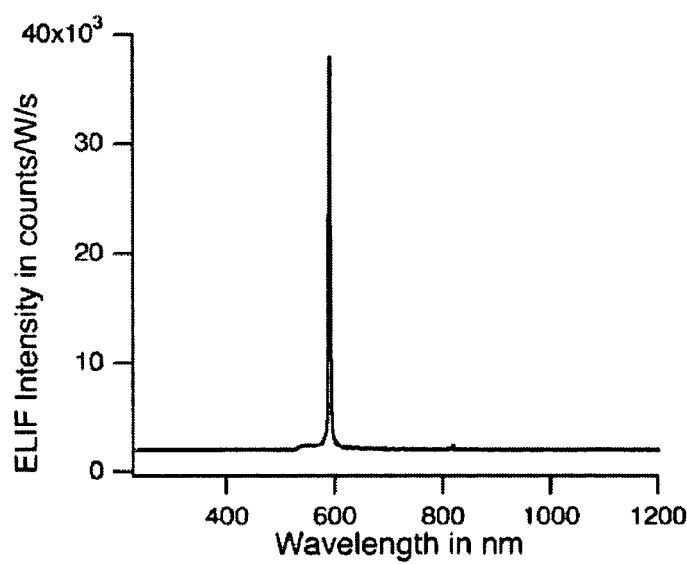

Because the temperature conditions in a typical oxy-fuel float glass furnace can range as high as 1700° C. and exhibit NaOH concentrations in the hundred-ppm range, the bench tests performed with the equipment shown in FIG. 2 were selected to span these conditions. FIG. 3B shows an ELIF spectrum of a 130-ppm NaOH sample in air at approximately 1000° C., and FIG. 3A at 1500° C., obtained in the tube furnace. While the 589 nm lines and the 819 nm lines are known to be closely spaced doublets, each appear as a single line due to the resolution limit of the spectrometer (1.9 nm). Note that the 819 nm line is very weak at the lower temperature. The signal-to-noise on the 589 nm line is approximately 550:1 with a data collection rate of 0.5 seconds.

Figure 4:
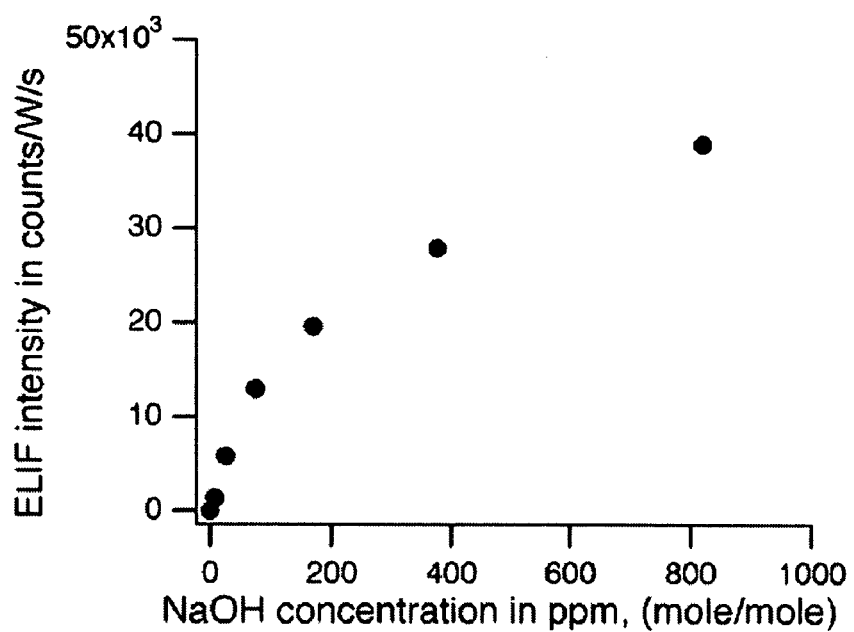
FIG. 4 shows the ELIF response at 589 nm as a function of NaOH concentration in nitrogen at 1500° C.

FIG. 4 shows a plot of the intensity dependence of the 589-nm line as a function of NaOH vapor concentration in the flow furnace at a temperature of about 1200° C. The response is nonlinear with a roll-off in the linearity of the response at higher NaOH concentrations. This curve is in excellent agreement with previously published data that describes the effect of radiation trapping at these high concentrations.

Figure 5:
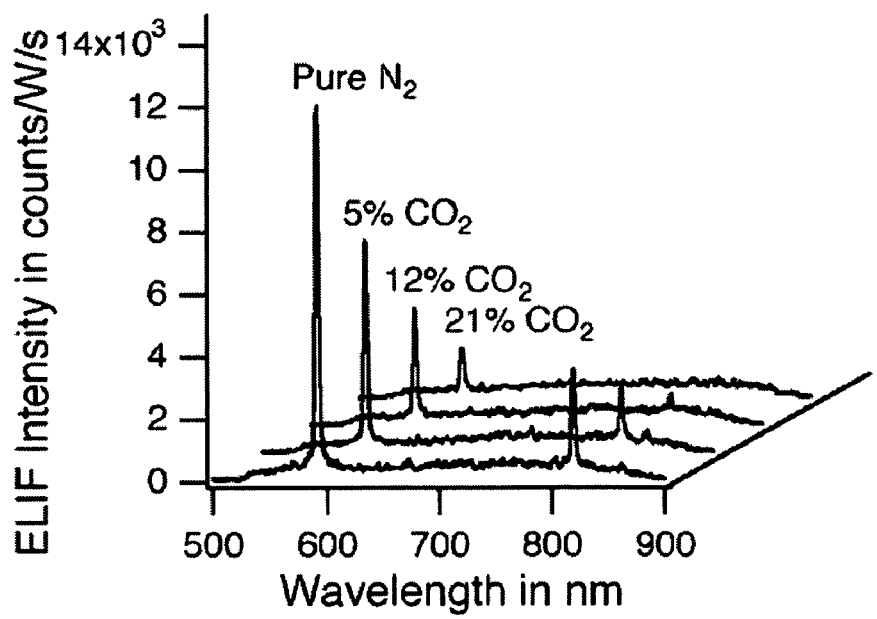
FIG. 5 shows the ELIF intensity as a function of $CO_2$ concentration in nitrogen at 1500° C.

The data obtained in the tube furnace calibrates the signal vs. concentration at a fixed pulse energy (100 µJ) and laser repetition rate in the well-controlled conditions of the laboratory tube furnace. The difficulty in developing a truly quantitative instrument is tied to the attenuation of the 193 nm laser beam by the intrinsic absorptivity of hot $CO_2$ (and to a lesser extent $O_2$) in the furnace atmosphere. For example, the reduction in overall signal intensity in FIGS. 3A and 3B at 1500° C. relative to 1000° C. is due to the increased attenuation of the excimer laser by oxygen in air at elevated temperature. Although the oxygen concentration is low in a furnace, a typical gas composition in an oxy-fired furnace contains greater than 30% $CO_2$. At temperatures above about 1200° C., beam attenuation due to $CO_2$ is significant and prevents, in a practical sense, being able to determine accurately the laser beam intensity within the detection volume. The net result is that the effective laser probe penetration depth into a furnace is less than one meter and is a strong function of temperature. FIG. 5 shows the effect on the ELIF signal at 1250° C. and 50-cm penetration into the calibration cell for different amounts of $CO_2$.

As a result of this beam attenuation issue, unless both the carbon dioxide partial pressure and the gas temperature are known very precisely, the ELIF signal cannot be accurately calibrated to make a quantitative determination of the NaOH concentration. However, the sensitivity and the stability of the ELIF approach make this method a very good candidate for a relative on-line measurement. That is, an instrument can be calibrated to a particular position in a furnace by taking a sample of the vapor and subsequently analyzing it. Such a measurement can then be used to show relative changes in NaOH concentration with very high time resolution as operating conditions within the furnace are tuned.

Portable Sensor Design

Figure 6:
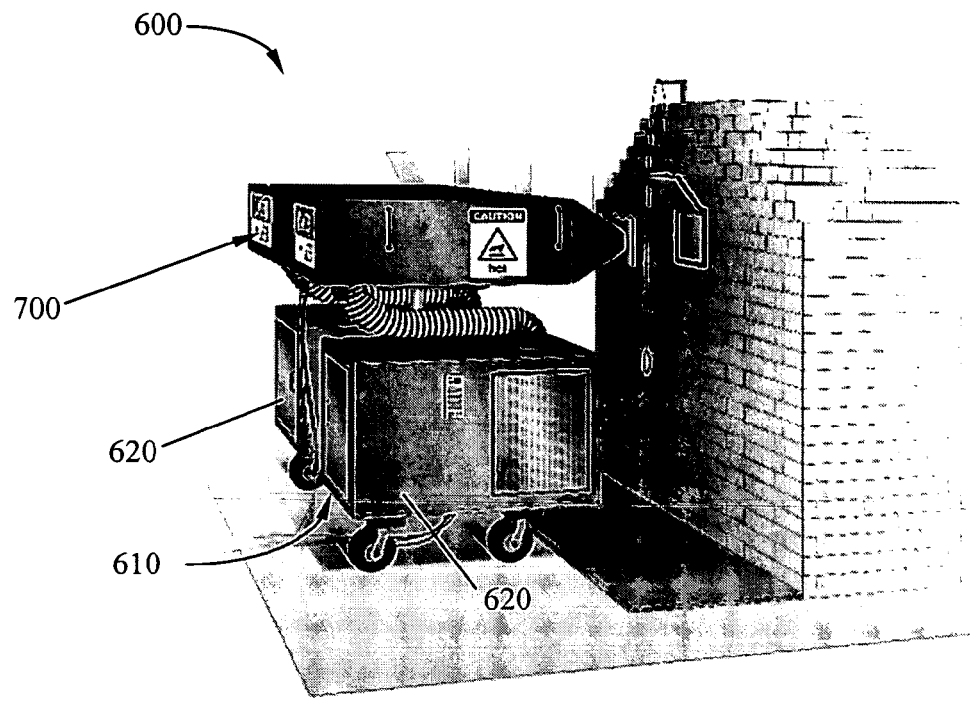
FIG. 6 depicts an illustration of the portable ELIF system at a furnace port, wherein the upper module sensor contains the sensors platform shown in FIG. 7.

FIG. 6 depicts a cartoon illustration of the fielded portable inspection system at a furnace port. Inspection system 600 was designed and constructed to explore the ELIF approach as a real time sensor in industrial settings utilizing large oxy-fired glass furnaces. To accomplish this task the system had to be reasonably portable for movement around hazards and obstacles and sufficiently rugged to be able to withstand the high ambient air temperatures adjacent to partially shielded glass melting tanks. The first field unit was comprised of enclosed optical sensor module 700 (depicted in schematic form in FIG. 7) supported by a wheeled hydraulic jack 610 (partially obscured). Jack 610 enables sensor module 700 to be positioned at elevations ranging from 45 inches to has high as 90 inches and tilted to point either up or down at an angle of up to ±20°. Sensor module 700 comprising the excimer laser, the detector, and imaging optics occupies a footprint about 0.7 m wide by about 1 m deep. It is supported by a pair of cabinets, or support modules 620, that house the electronics needed to operate the detector along with two air conditioners that provide forced air to cool the laser and detection electronics. In addition, both sensor and support modules 700 and 620 are entirely enclosed in an insulated compartment (depicted as reference 710 in FIG. 7) constructed from sheet metal panels 712 that sandwich 1-inch insulation blankets 714 to provide thermal protection for the equipment.

Figure 7:
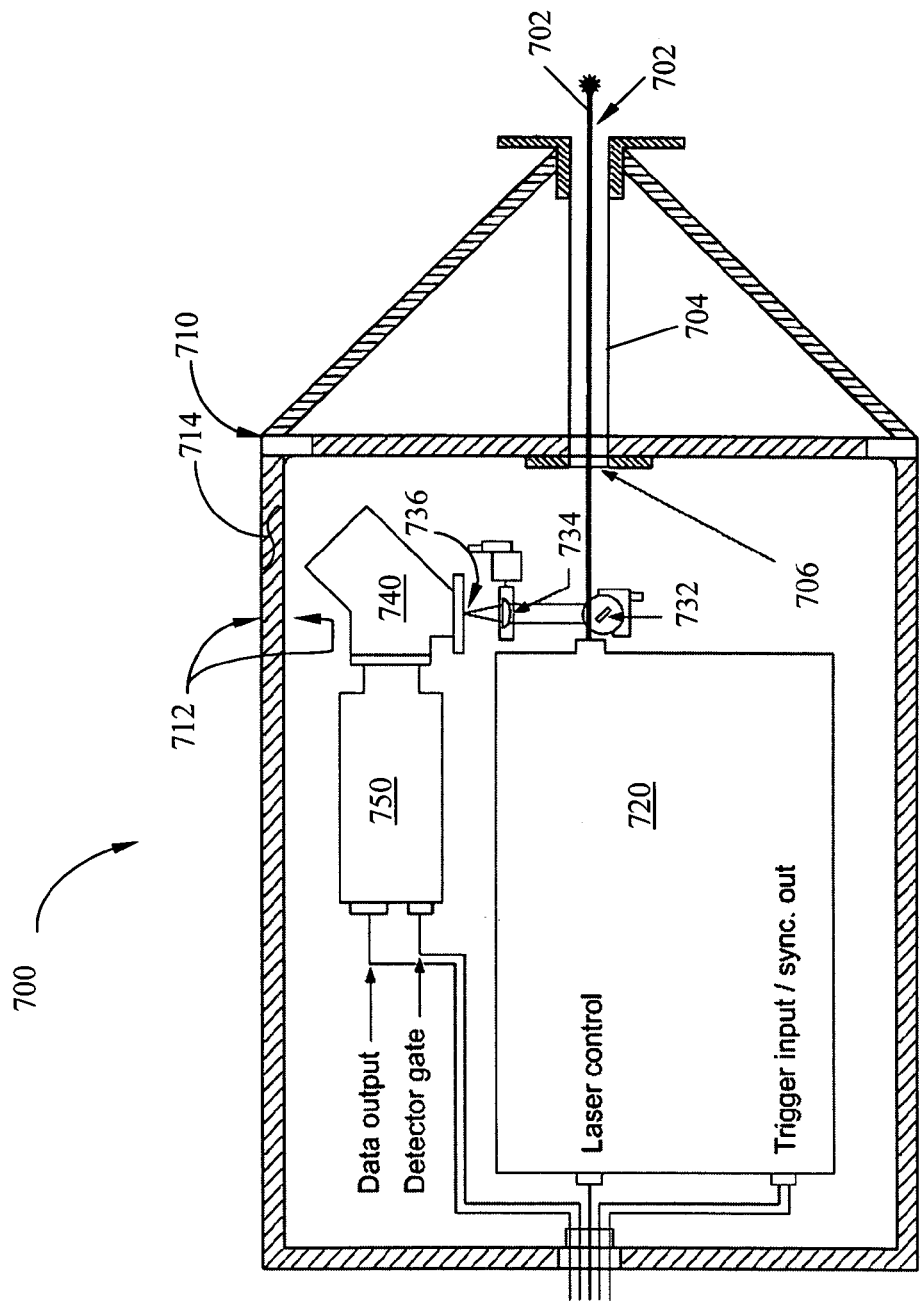
FIG. 7 illustrates a schematic of the sensor module layout.

The layout schematic of sensor module 700 is shown in FIG. 7 and comprises of an optical configuration comprising ArF excimer laser 720 operated at 100 Hz and produces a 12 ns pulse. The 193-nm ultraviolet light beam 722 output from laser 720 dissociates the NaOH species in the vapor phase and produces sodium atoms that subsequently fluoresce at several possible wavelengths. Fluorescent light 724 is collected and redirected by an off-axis light collection system, comprising mirror 732 mounted on a rotatable stage (not shown) and focusing lens 734 that images light 724 into 0.025 mm slit 736 and ultimately into spectrometer 740 where the light is dispersed into a spectrum and detected by intensified (50 ns gate) multi-channel diode array (or multi-channel intensified CCD array) 750 that provides an electronic output proportional to the intensity of the spectrum over a wavelength range between about 400 nm to about 1200 nm.

Figure 8:
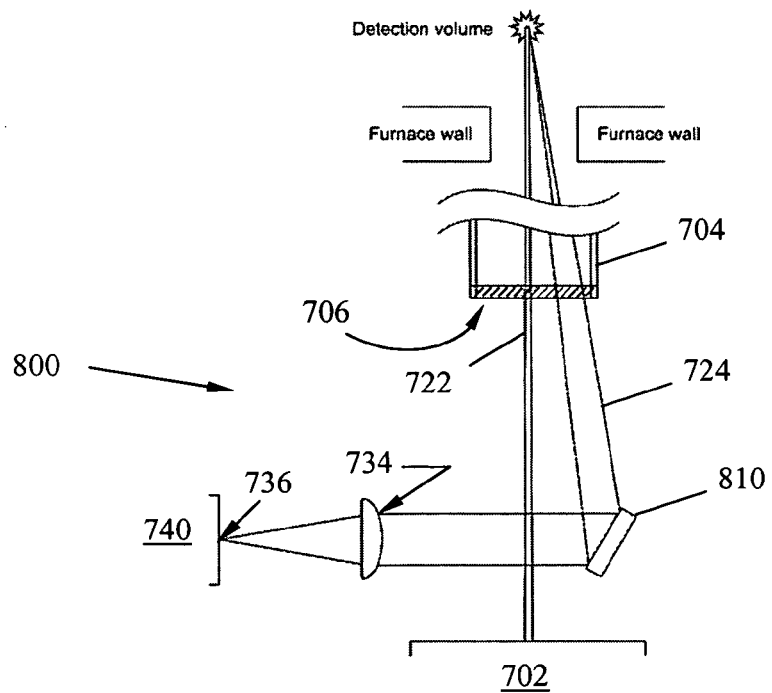
FIG. 8 shows the geometry of the off-axis imaging of the NaOH ELIF signal of the sensors platform shown in FIG. 7.

The output of excimer laser 720 is centered on a 5-cm diameter aperture 702 formed by observation tube 704, roughly ⅓ meter in length, and by UV fused silica window 706. Tube 704 serves as a portal both for pulse laser output beam 722 and signal response 724, collected off axis, and provides "stand off" from the intense heat emanating from any of the glass furnace inspection ports. FIG. 8 shows a schematic of light collection scheme 800. This simple single lens imaging system is configured with mirror 810 mounted on rotatable stage (not shown) that is configured to image any point along laser beam 722 ranging from just beyond the end of tube 704 out to a point about four meters from sensor module 600. Simple geometric instruction shows that mirror 810, offset by about 1.5 cm from the centerline of laser beam 722, needs to be shifted through an angle of only about 0.65° to about 1° in order to shift the inspection point from about 1 meter to about 4 meters from sensor module 600 in order to direct the observed ELIF signal into fixed slit 736. While rotatable stage was equipped with a micrometer that provided only about 5 arc-minute resolution (±0.08°) capability, piezoelectric kinematic mounts are available that can increase this resolution to about 30 arc-seconds (±0.008°).

EXAMPLES

Field Tests

The first field tests were conducted at a small batch glass furnace at the University of Missouri at Rolla ("Rolla"). For these tests, the single burner furnace was operated in an oxy-fuel mode maintained at 1500° C. Feed mix including "cullet" (waste or broken glass suitable for re-melting) was added in regular batches that contained measured amounts of sodium carbonate. Typical batch operation consisted of adding a 1-kg bag of feedstock every 15 minutes that comprised 42 wt % $SiO_2$; 14 wt % $Na_2CO_3$; 3.5 wt % $CaCO_3$; 9.8 wt % dolomite; 0.7 wt % gypsum; and 30 wt % cullet. $Na_2CO_3$ was added to enhance the NaOH concentration in the chamber. Glass can be removed from the base of the tank, however, during this testing; the glass melt was simply allowed to accumulate. Because of its small size and lower operating temperature the ambient temperature of the Rolla furnace was only 55° C. at a distance of 20 cm from the furnace, and 35° C. at a distance of 1 meter.

Figure 9:
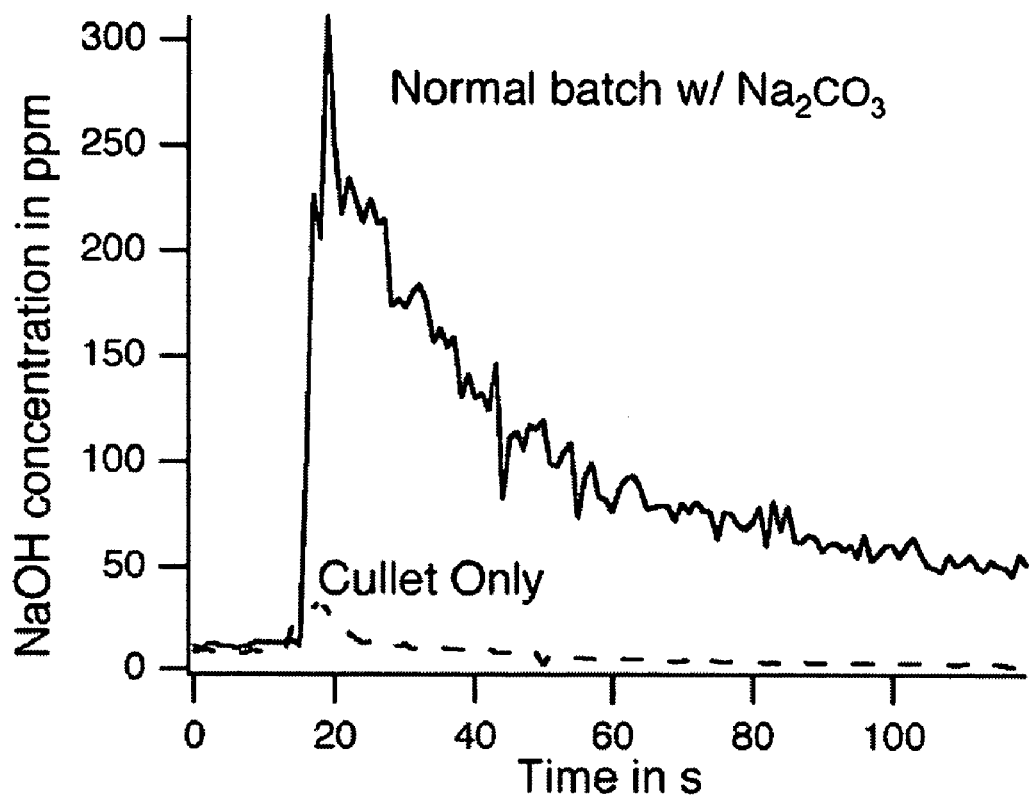
FIG. 9 shows a comparison of the absolute sodium concentration in the batch furnace atmosphere after an addition of a normal 1 kg batch w/14% $Na_2CO_3$ and after "blank" batch containing only cullet.

These initial tests were used to evaluate the durability of the unit when operated adjacent to a furnace port. The instrument was calibrated using the tube furnace configuration for a focal point about 40 cm in front of the heat shield, locating the sample volume approximately 5 cm inside the inner wall of the furnace. The sodium hydroxide ELIF signal was recorded as a function of time following the addition of each batch. The evolution of the ELIF spectrum is shown in FIG. 9. The conversion from ELIF signal to ppm (mole/mole) is taken from the calibration procedure conducted in the tube furnace in FIG. 4. At approximately 16 seconds, a batch of feed mix (including the sodium carbonate) is added to the melt. The ELIF signal increases dramatically and then begins to taper off. FIG. 9 compares a normal batch feed with feed that contained only cullet. The "cullet only" tests were conducted to provide assurance that the ELIF system was truly detecting the presence of NaOH in the vapor and not erroneously measuring some other effect from the batching procedure such as a disturbance in the gas flow field in the furnace that resulted in a boost in the background NaOH signal.

Figure 10:
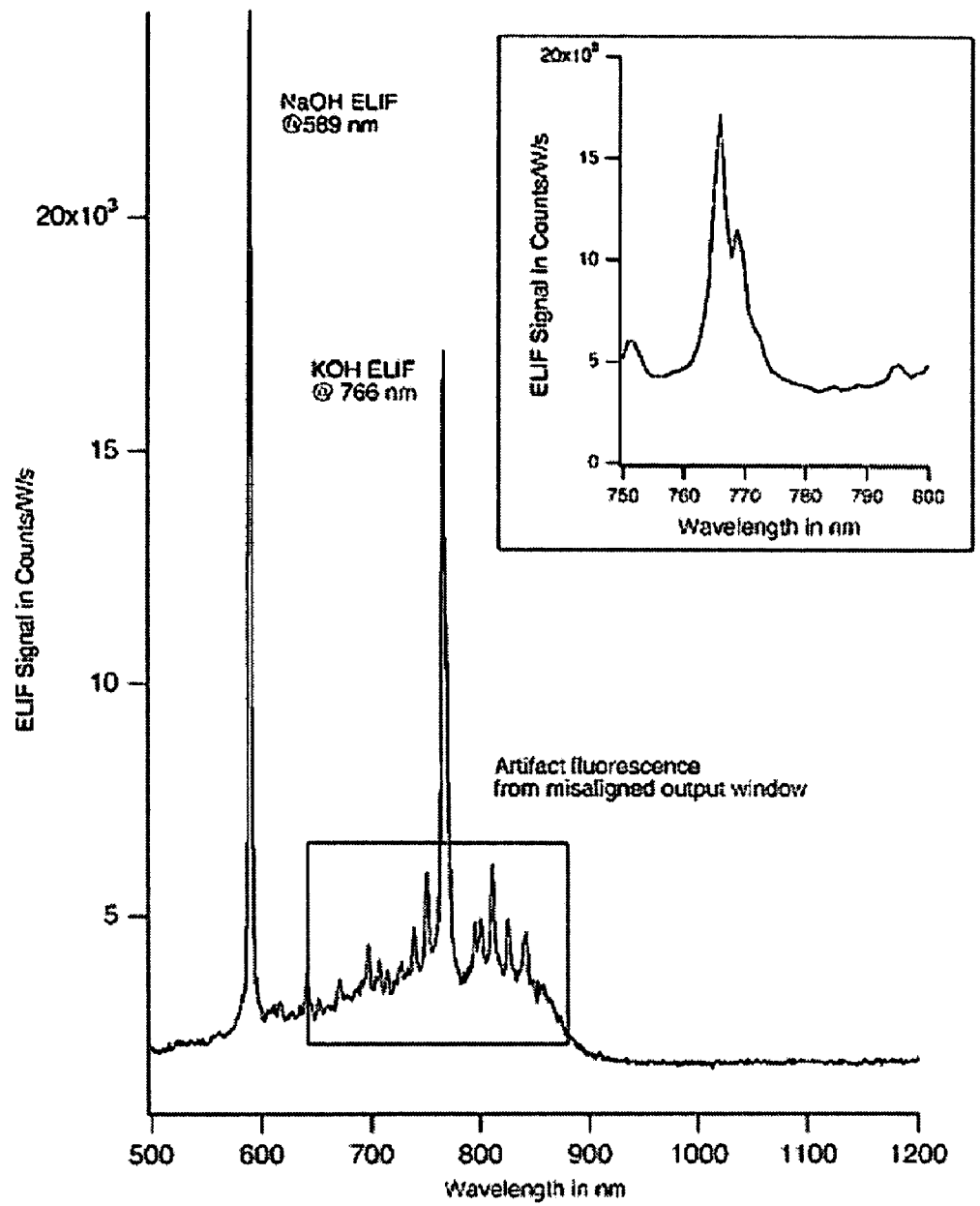
FIG. 10 illustrates the ELIF signal in the batch furnace from the addition of a mixture containing both sodium and potassium carbonate. The inset shows the resolution of the potassium doublet at 766.5 nm and 769.9 nm.

FIG. 10 shows a sample ELIF scan of a batch that contained both $Na_2CO_3$ and $K_2CO_3$. Note the prominent signal at 768 nm due to the ELIF signal from KOH. Although calibration curves for the KOH signal were not developed, it is clear that both sodium and potassium can be monitored simultaneously. The inset shows the KOH feature to be the pair of atomic lines in the potassium atomic spectrum ($4p^2P_{3/2,1/2}$–$4s^2S$) at 766.5 nm and 769.9 nm.

As a result of the batch furnace tests at Rolla, the sensor system underwent several modifications with respect to the cooling system and was taken to a commercial float glass plant. The purpose of this series of tests was twofold: the first goal was to assess the durability of the instrument in an actual industrial environment, and the second was to compare the results of the ELIF method to a set of extractive atmospheric samples taken from the operating industrial furnace.

From a durability standpoint there are two primary constraints. The laser cannot operate at temperatures above 40° C. and the detector temperature must be maintained (thermoelectrically) at a temperature below about –20° C. It is important to note that the air temperature 1 meter from the furnace wall is approximately 90° C. Moreover, when the glass furnace is operating at 1500° C., the radiant heat flux entering the sensor head through the 5 cm diameter optical port is approximately 60 W/cm², resulting in an energy load of nearly 1200 W that must be removed from the interior of the sensor system by the air conditioning unit. In general, the portable unit performed well, although it was found that the unit began to overheat if it remained directly in front of an open furnace inspection port for more than about twenty minutes.

Figure 11A:
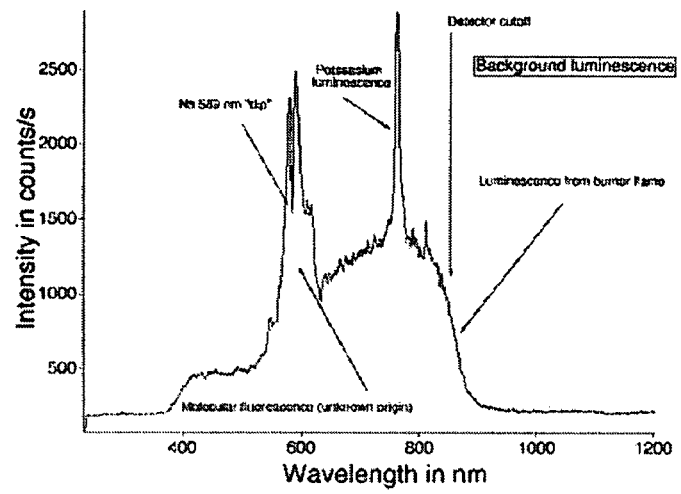
FIG. 11A shows the background fluorescence in a melt tank.
Figure 11B:
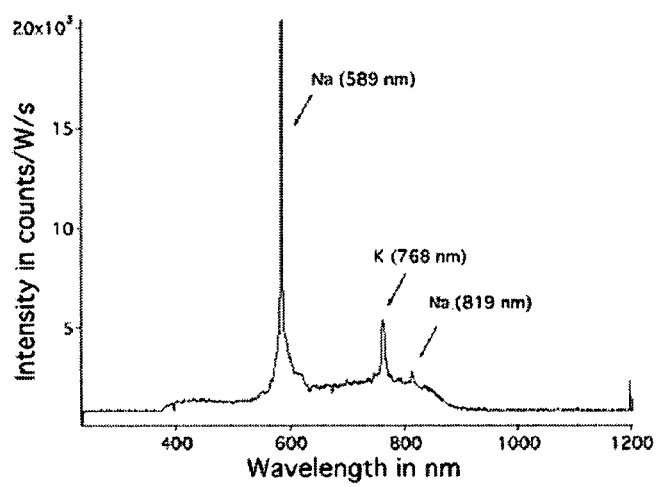
FIG. 11B shows the ELIF signal from a tank peephole.
Figure 11C:
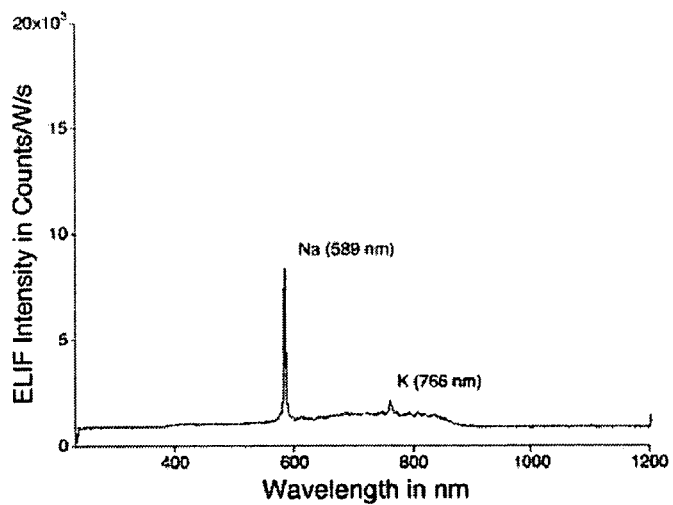
FIG. 11C shows the ELIF signal from an exhaust peephole.

FIGS. 11A–11C show three typical data sets recorded during these field trials. FIG. 11A shows the background fluorescence signal recorded through a peephole, located about mid-tank, which permits visual access directly into the melt tank. FIG. 11B shows the corresponding ELIF signal recorded at the same peephole. FIG. 11C shows the ELIF signal recorded in an exhaust vent about 20 feet down tank from the position in FIGS. 11A and 11B. The background fluorescence is much greater than in the batch furnace at Rolla and contains additional features. This large background is present primarily because the peephole view is directly opposite a burner. Note the broad fluorescence in the region of the 589 nm sodium line and the very sharp dip in this fluorescence due to the absorption by ground state sodium atoms along the optical path from the burner flame to the detector. There is also atomic emission from volatilized potassium as well. Although the ELIF signal at 589 nm peering directly into the tank is stronger than the signal in the exhaust, it is complicated by the broad feature in the background spectrum. The exhaust ELIF signal is cleaner and looks identical to the 589 nm spectra that were obtained in the lab and in the batch furnace at Rolla. That is, there is no interfering atomic sodium emission from the burners. This was also the case for ELIF data recorded directly at the mouth of the furnace above the feeder. Clearly the ELIF method can be used to produce strong NaOH signals with the sensor unit adjacent to the melt tank, but it appears the analysis and conversion using a calibration curve will be much simpler when monitoring the exhaust.

Samples of the furnace composition were obtained using a commercial stack sampling system (Andersen Instruments MST) in order to determine the quantitative accuracy of the ELIF method relative to direct sampling. The technique consisted of drawing approximately 0.3 m³ of gas (dry) from the furnace using an alumina probe and condensing out the water vapor in a series of chilled vessels. The water content of the samples was determined using EPA Method #4. The accumulated condensate is then subsequently analyzed for its composition using a direct current plasma emission technique. In this way, the sodium concentration was determined directly to serve as a comparison to the ELIF measurements using the calibration shown in FIG. 4.

TABLE 1

-ELIF NaOH Measurements and Results of Extractive Sampling

| Furnace Inspection Port Position | Extraction Sample Na concentration (ppm, male/mole) | ELIF NaOH concentration (ppm, mole/mole)$^a$ |
|---|---|---|
| 1. Right side mid-tank port | 185 | 125 |
| 2. Right side exhaust port | 202 | 117 |
| 3. Right side up-tank port | 158 | 143 |
| 4. Feeder | n.a. | 90 |
| 5. Left side down-tank port | 221 | 31 |
| 6. Left side Refiner | 17 | n.a. |

$^a$using calibration in FIG. 4;
n.a. means not available due to tank access constraints The results of these sampling tests are shown above in Table 1. The time averaged ELIF concentrations are in the appropriate range with the exception of position 5. The missing data for the ELIF method on the refiner and for the extraction probe on the feeder are the result of physical access constraints in the actual environment. Considering the beam attenuation uncertainties and the time dependent fluctuations of the actual concentration of NaOH itself, this agreement is considered to be fairly good for a "first generation" instrument (again, with the exception of the position 5 measurement).

We claim:
1. An Excimer Laser Induced Fragmentation Fluorescence (ELIF) stand-off probe, comprising:
   a high intensity laser, said laser providing a high intensity light beam;
   a fused silica or fused glass window through which said light beam passes;
   a spectrometer having a light receiving aperture;
   a slit mounted over said light receiving aperture;
   a light collecting means comprising a mirror mounted on a rotatable stage and at least one focusing lens, said light collecting means disposed adjacent to said light beam, wherein said light collecting means images a predefined region in space along said light beam and gathers light generated by a photo-dissociation reaction between said light beam and any of a population of molecular species occupying said region of space traversed by said light beam, said mirror directing said generated light into said lens, wherein said lens focuses said generated light onto said slit and thence into said spectrometer, wherein said spectrometer disperses said generated light into a light spectrum; and
   means for detecting for said light spectrum and providing an electronic output signal proportional to said light spectrum over a wavelength range of between about 400 nm to about 1200 nm.

2. The ELIF stand-off probe of claim 1, further comprising an insulated housing.

3. The ELIF stand-off probe of claim 2, wherein the insulated housing comprises an interior cooling means.

4. The ELIF stand-off probe of claim 2, wherein said insulated housing is maintained at a temperature below 40° C.

5. The ELIF stand-off probe of claim 1, wherein the rotatable stage is capable of an angular resolution of about 0.08° (±0.04°).

6. The ELIF stand-off probe of claim 5, wherein the rotatable stage comprises a mechanical or an electrical rotation means.

7. The ELIF stand-off probe of claim 6, wherein the rotation means comprises a micrometer.

8. The ELIF stand-off probe of claim 6, wherein the rotation means comprises a closed-loop motorized actuator.

9. The ELIF stand-off probe of claim 8, wherein the closed-loop motorized actuator comprises a piezoelectric actuator.

10. The ELIF stand-off probe of claim 6, wherein the rotation means comprises a micrometer and a closed-loop motorized actuator.

11. The ELIF stand-off probe of claim 10, wherein the rotation means comprises a micrometer and a closed-loop motorized piezoelectric actuator.

12. The ELIF stand-off probe of claim 1, wherein said means for the detecting comprises a multi-channel light detector.

13. The ELIF stand-off probe of claim 12, wherein the multi-channel light detector comprises a charge coupled device ("CCD") array.

14. The ELIF stand-off probe of claim 13, wherein the CCD array is an intensified multi-channel diode-array.

15. The ELIF stand-off probe of claim 13, wherein the CCD array is an intensified multi-channel CCD array.

* * * * *